United States Patent
Jeschke et al.

(10) Patent No.: US 7,763,640 B2
(45) Date of Patent: *Jul. 27, 2010

(54) SUBSTITUTED OXYGUANIDINES

(75) Inventors: Peter Jeschke, Bergisch Gladbach (DE); Peter Lösel, Leverkusen (DE); Ralf Nauen, Langenfeld (DE); Peter Marczok, Köln (DE); Christian Arnold, Langenfeld (DE); Erich Sanwald, Kiel (DE)

(73) Assignee: Bayer CorpScience AG, Monheim (DE)

( * ) Notice: Subject to any disclaimer, the term of this patent is extended or adjusted under 35 U.S.C. 154(b) by 64 days.

This patent is subject to a terminal disclaimer.

(21) Appl. No.: 11/791,334

(22) PCT Filed: Nov. 12, 2005

(86) PCT No.: PCT/EP2005/012149

§ 371 (c)(1),
(2), (4) Date: Apr. 21, 2008

(87) PCT Pub. No.: WO2006/056333

PCT Pub. Date: Jun. 1, 2006

(65) Prior Publication Data

US 2008/0312297 A1    Dec. 18, 2008

(30) Foreign Application Priority Data

Nov. 24, 2004   (DE) .................. 10 2004 056 626

(51) Int. Cl.
| | |
|---|---|
| A61K 31/44 | (2006.01) |
| A61K 31/425 | (2006.01) |
| C07D 213/57 | (2006.01) |
| C07D 227/28 | (2006.01) |
| A01N 43/40 | (2006.01) |
| A01N 43/36 | (2006.01) |

(52) U.S. Cl. ............ 514/357; 514/365; 546/330; 504/130; 504/138; 548/205

(58) Field of Classification Search ............ 548/205; 546/338, 330; 504/130, 138; 514/357, 365
See application file for complete search history.

(56) References Cited

U.S. PATENT DOCUMENTS

| 5,245,040 A | 9/1993 | Maienfisch et al. |
|---|---|---|
| 5,434,181 A | 7/1995 | Kodaka et al. |
| 6,103,763 A * | 8/2000 | Horst .................. 514/547 |
| 6,194,575 B1 | 2/2001 | Wollweber et al. |
| 6,534,529 B2 * | 3/2003 | Uhr et al. .................. 514/341 |
| 6,828,275 B2 | 12/2004 | Uhr et al. |
| 2005/0009883 A1 | 1/2005 | Uhr et al. |
| 2008/0261810 A1 | 10/2008 | Fischer et al. |
| 2009/0105235 A1 * | 4/2009 | Jeschke et al. ............ 514/229.2 |
| 2009/0270254 A1 | 10/2009 | Thielert et al. |
| 2009/0298888 A1 | 12/2009 | Thielert et al. |

FOREIGN PATENT DOCUMENTS

| EP | 0 375 907 A1 | 7/1990 |
|---|---|---|
| EP | 0 376 279 A2 | 7/1990 |
| EP | 0 425 978 A2 | 5/1991 |
| EP | 0 452 782 A1 | 10/1991 |
| EP | 0 483 062 A2 | 4/1992 |
| EP | 0 649 845 A1 | 4/1995 |
| WO | WO 98/42690 A1 | 10/1998 |

OTHER PUBLICATIONS

International Search Report for International Application No. PCT/EP2005/012149, European Patent Office, mailed on Jan. 30, 2006.

* cited by examiner

*Primary Examiner*—Janet L Andres
*Assistant Examiner*—Binta M Robinson
(74) *Attorney, Agent, or Firm*—Sterne, Kessler, Goldstein & Fox P.L.L.C.

(57) ABSTRACT

The present application relates to new substituted oxyguanidines of structure (I)

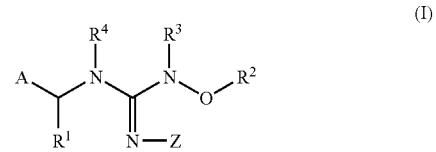

a method for their preparation and their use for the control of animal pests, mainly arthropods, in particular insects.

5 Claims, No Drawings

SUBSTITUTED OXYGUANIDINES

CROSS-REFERENCE TO RELATED APPLICATIONS

This is the U.S. National Stage of WO application number PCT/EP2005/012149, filed Nov. 12, 2005, now pending, which claims priority from DE 10 2004 056 626.7 filed Nov. 24, 2004, each of which is wholly incorporated by reference herein.

The present application relates to new substituted oxyguanidines, a method for their preparation and their use for the control of animal pests, mainly arthropods, especially insects.

A series of N-alkyl-N'-nitroguanidines is already known as insecticidally active compounds (cf. EP-375907, EP-376279, EP-425978, EP-483062).

An example of an N-alkoxy-N'-nitroguanidine is also known in the form of the compound N-methoxy-N'-nitro-N''-(tetrahydro-3-furanylmethyl)guanidine (cf. EP-649845).

New compounds of structure (I) have been found,

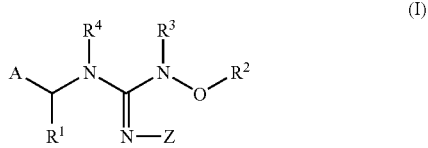

(I)

in which
A stands for in each case optionally substituted aryl or heteroaryl and—where Z stands for cyano—also for optionally substituted tetrahydrofuryl,
$R^1$ stands for hydrogen or alkyl,
$R^2$ stands for hydrogen or alkyl,
$R^3$ stands for hydrogen or alkyl,
$R^4$ stands for hydrogen, alkyl or cycloalkyl, and
Z stands for cyano or nitro.

It has been further found that the new substituted oxyguanidines of structure (I) are obtained if isothioureas of structure (II)

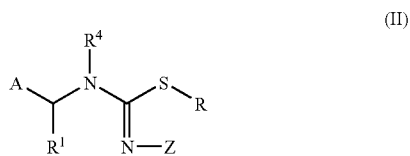

(II)

in which
A, $R^1$, $R^4$ and Z have the above described meaning and
R stands for alkyl,
are reacted with oxyamines of structure (III)

(III)

in which
$R^2$ and $R^3$ have the above described meaning
or with acid adducts of the compounds of structure (II), such as, for example their hydrochlorides optionally in the presence of a basic reaction auxiliary and optionally in the presence of a diluent.

Finally it was found that the new compounds of structure (I) possess pronounced biological properties, and are suitable above all for the control of animal pests, especially insects, arachnids and nematodes that occur in agriculture, forestry, storage and materials protection as well as in the hygiene sector.

Depending upon the nature of the substituents the compounds of structure (I) may exist as geometric and/or as optically active isomers or corresponding isomer mixtures of different composition. The invention relates to both the pure isomers as well as the isomer mixtures.

The compounds of the invention are defined in general terms by structure (I).

Preferred substituents and ranges of the residues in the structures mentioned above and hereafter are defined in the following.

A stands preferably for phenyl optionally substituted by halogen, cyano, nitro, $C_1$-$C_4$-alkyl, $C_1$-$C_4$-haloalkyl, $C_1$-$C_4$-alkoxy or $C_1$-$C_4$-haloalkoxy.

A stands preferably also for pyrazolyl, 1,2,4-triazolyl, oxazolyl, isoxazolyl, thiazolyl, isothiazolyl, 1,2,5-thiadiazolyl, pyridyl, pyrazinyl or pyrimidinyl which are optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine) or $C_1$-$C_2$-alkylsulphonyl (which is optionally substituted by fluorine and/or chlorine).

A stands preferably also for tetrahydrofuryl, optionally substituted by $C_1$-$C_4$-alkyl, where Z stands for cyano.

$R^1$ stands preferably for hydrogen or methyl, ethyl or n-propyl or iso-propyl.

$R^2$ stands preferably for hydrogen, methyl, ethyl, n-propyl or n-butyl.

$R^3$ stands preferably for hydrogen, methyl, or ethyl.

$R^4$ stands preferably for hydrogen, methyl, ethyl, n- or iso-propyl, cyclopropyl, cyclobutyl, cyclopentyl or cyclohexyl.

Z stands preferably for cyano or nitro.

A stands more preferably for thiazolyl or pyridyl, which are optionally substituted by halogen (especially chlorine) or $C_1$-$C_3$-alkyl (especially methyl).

$R^1$ stands more preferably for hydrogen or methyl.

$R^2$ stands more preferably for hydrogen, methyl, ethyl or n-propyl.

$R^3$ stands more preferably for hydrogen or methyl.

$R^4$ stands more preferably for hydrogen, methyl, ethyl or cyclopropyl.

Z stands more preferably for cyano or nitro.

A stands most preferably for 2-chloropyridin-5-yl or 2-chloro-1,3-thiazol-5-yl.

$R^1$ stands most preferably for hydrogen.

$R^2$ stands most preferably for methyl.

$R^2$ stands most preferably also for ethyl.

$R^3$ stands most preferably for hydrogen.

$R^4$ stands most preferably for hydrogen.

Z stands most preferably for nitro.

In a particularly highlighted group of compounds of structure (I) A stands for 2-chloropyridin-5-yl

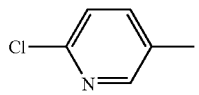

In a further particularly highlighted group of compounds of structure (I) A stands for 2-chloro-1,3-thiazol-5-yl

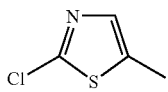

According to the invention compounds of structure (I) are preferred in which combinations of the aforementioned meanings listed as preferred are present.

According to the invention compounds of structure (I) are more preferred in which combinations of the aforementioned meanings listed more preferred are present.

According to the invention compounds of structure (I) are most preferred in which combinations of the aforementioned meanings listed as most preferred are present.

In the above and hereafter listed residue definitions hydrocarbon residues such as alkyl—also in association with heteroatoms such as alkoxy—are where possible in each case straight-chain or branched.

If, for example, N-nitro-N'-(2-chloro-pyridin-5-ylmethyl)-S-methylisothiourea and O-methylhydroxylamine are used as starting materials the course of the reaction of the invention can be outlined by the following scheme:

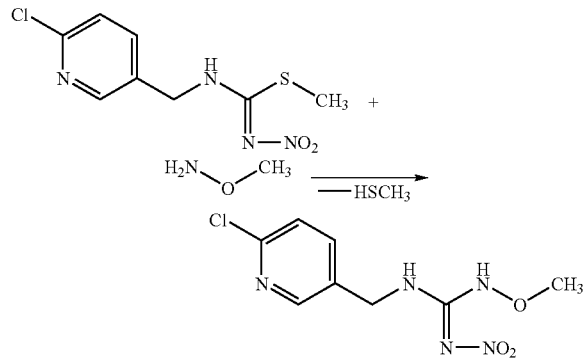

The isothioureas used as starting materials in the method of the invention for the preparation of the compounds of general structure (I) are defined in general by the structure (II). In the general structure (II) A and $R^1$ have preferably or more preferably those meanings that have already been given above as respectively preferred or more preferred for A and R' in connection with the description of the compounds of the invention of structure (I); R stands for alkyl, preferably for alkyl with 1 to 4 carbon atoms, especially for methyl or ethyl.

The starting materials of the general structure (II) are known and/or can be prepared by known methods (cf. EP-452782).

The oxyamines used as starting materials in the method of the invention for the preparation of the compounds of general structure (I) are defined in general by the structure (III). In the general structure (III) $R^2$ and $R^3$ have preferably or more preferably those meanings that have already been given above as respectively preferred or more preferred for $R^2$ and $R^3$ in connection with the description of the compounds of the invention of structure (I);

The starting materials of general structure (III) are known synthetic organic chemicals.

All suitable inorganic and organic acid acceptors can be used as basic reaction auxiliaries in carrying out the method of the invention. These include preferably alkali metal and alkaline earth metal compounds as well as basic nitrogen compounds, especially alkylamines.

Named as examples are the hydroxides, oxides and carbonates of lithium, sodium, potassium, magnesium, calcium and barium, in addition further basic compounds such as amidine bases or guanidine bases such as 7-methyl-1,5,7-triazabicyclo(4.4.0)-dec-5-ene (MTBD), diazabicyclo(4.3.0)nonene (DBN), diazabicyclo(2.2.2)octane (DABCO), 1,8-diazabicyclo(5.4.0)undecene (DBU), cyclohexyltetrabutylguanidine (CyTBG), cyclohexyltetramethylguanidine (CyTMG), N,N,N,N-tetramethyl-1,8-naphthalinediamine, pentamethylpiperidine, tertiary amines such as triethylamine, trimethylamine, tribenzylamine, triisobutylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrrole, N-methylmorpholine, N-methylhexamethylenimine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine.

Preferably used are tertiary amines, especially trialkylamines such as triethylamine, N,N-diisopropylamine, N-propyldiisopropylamine, N,N'-dimethylcyclohexylamine or N-methylmorpholine.

All solvents that are inert under the reaction conditions can be used as diluents in carrying out the method of the invention.

Named as examples are: halohydrocarbons, especially chlorohydrocarbons such as tetrachlorethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols such as methanol, ethanol, isopropanol, butanol; ethers such as ethylpropyl ether, methyl-tert-butyl ether, n-butyl ether, anisole, phenethol, cyclohexylmethyl ether, dimethyl ether, diethyl ether, dipropyl ether, diisopropyl ether, di-n-propyl ether, diisobutyl ether, diisoamyl ether, ethyleneglycoldimethyl ether, tetrahydrofuran, dioxan, dichlorodiethyl ether and polyethers of ethylene oxide and/or propylene oxide; amines such as trimethyl-, triethyl-, tripropyl-, tributylamine, N-methylmorpholine, pyridine and tetramethylene-diamine, nitrohydrocarbons such as nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile as well as compounds such as tetrahydrothiophenoxide and dimethyl sulphoxide, tetramethyl sulphoxide, dipropyl sulphoxide, benzylmethyl sulphoxide, diisobutyl sulphoxide, dibutyl sulphoxide, diisoamyl sulphoxide; sulphones such as dimethyl, diethyl, dipropyl, dibutyl, diphenyl, dihexyl, methylhexyl, ethylpropyl, ethylisobutyl and pentamethylene sulphone; aliphatic, cycloaliphatic or aromatic hydrocarbons for example so-called, white spirits with components with boiling points in the range for example of 40° C. to 250° C., cymol, petroleum fractions within a boiling range of 70° C. to 190° C., cyclohexane, methylcyclohexane, petroleum ether, ligroin, octane, benzene, toluene, chlorobenzene, bromobenzene, nitrotoluene, xylene; esters such as methyl, ethyl, butyl, isobutyl acetate as well as dimethyl, dibutyl, ethylene carbonate; amides such as hexamethylene-phosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidine, octylcaprolactam, 1,3-dimethyl-2-imidazolinedione, N-formylpiperidine, N,N'-1,4-diformylpiperazine; ketones such as acetone, acetophenone, methylethylketone, methylbutylketone, water.

It is also possible of course to carry out the method of the invention in mixtures of the named solvents and diluents.

Preferred diluents are, however, alcohols, for example methanol or ethanol, optionally in admixture with water.

When carrying out the method of the invention the reaction temperatures can be varied over a wide range. In general temperatures between −50° C. and +100° C., preferably between −30° C. and +150° C., especially between −15° C. and +80° C., are used.

The method of the invention is generally carried out under normal pressure. However, it is possible to carry out the method of the invention under elevated or reduced pressure—generally between 0.1 and 15 bar.

In carrying out the method of the invention the starting materials are generally used in approximately equimolecular amounts. However, it is possible to use one of the components in a larger excess. In general the reaction is carried out in a suitable diluent in the presence of a reaction auxiliary, optionally also in a protective atmosphere (for example, under nitrogen, argon or helium) and generally the reaction mixture is stirred for several hours at the required temperature. Work-up is carried out by normal methods (cf. the preparation examples).

Alternatively the preparation of the compounds of structure (I) of the invention can also be carried out from compounds of the general structure (IV)—in which $R^4$ stands for hydrogen—by known literature methods; for example the hexahydro-1,3,5-triazine system can be cleaved according to the following scheme in the presence of acidic reaction auxiliaries (cf. Tetrahedron Lett. 41, 7187-7191, 2000) or basic reaction auxiliaries, in the presence of urea (cf. WO-98/42690) or primary amines (cf. DE-19806469).

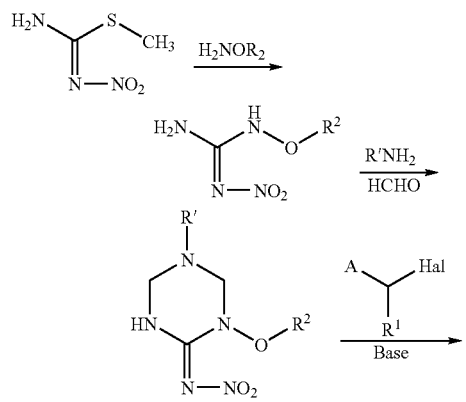

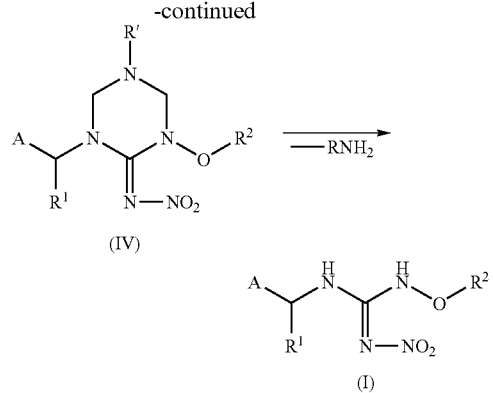

The compounds required here as starting materials can be defined by the general structure (IV). In the structure (IV) A, $R^1$ and $R^2$ stand preferably for those residues that have already been named as preferred substituents in connection with the description of the compounds of the invention of structure (I). Furthermore the residue R' in structure (IV) stands for an alkyl or aralkyl group.

The compounds of structure (I) can optionally exist as different polymorphic forms or as mixtures of different polymorphic forms. Both the pure polymorphs and the polymorph mixtures are subject matter of this invention and can be used according to the invention.

The active compounds of the invention with good plant tolerance, favourable mammalian toxicity and good environmental compatibility are suitable for the protection of plants and plant organs, for increasing yields, improvement in quality of the produce and for the control of animal pests, especially insects, arachnids, helminths, nematodes and molluscs that occur in agriculture, horticulture, in animal breeding, in forestry, in garden and leisure facilities, in storage and material protection and in the hygiene sector. They can be used advantageously as plant protection agents. They are active against normal sensitive and resistant species as well as against all or individual developmental stages. The above named pests include:

the order of Anoplura (Phthiraptera) e.g. *Damalinia* spp., *Haematopinus* spp., *Linognathus* spp., *Pediculus* spp., *Trichodectes* spp.; the class of *Arachnida* e.g. *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*;

the class of Bivalva e.g. *Dreissena* spp.;

the order of Chilopoda e.g. *Geophilus* spp., *Scutigera* spp.;

the order of Coleoptera e.g. *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp.,

*Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnostema consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

the order of *Collembola* e.g. *Onychiurus armatus;* the order of *Dermaptera* e.g. *Forficula auricularia;* the order of *Diplopoda* e.g. *Blaniulus guttulatus;* the order of *Diptera* e.g. *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.; the class of *Gastropoda* e.g. *Arion* spp., *Biomphalaria* spp., *Bulinus* spp., *Deroceras* spp., *Galba* spp., *Lyrnnaea* spp., *Oncomelania* spp., *Succinea* spp.; the class of helminths e.g. *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.* Furthermore protozoa such as Eimeria may be controlled.

The order of *Heteroptera* e.g. *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

the order of *Homoptera* e.g. *Acyrthosipon* spp., *Aeneolamia* spp., *Agonoscena* spp., *Aleurodes* spp., *Aleurolobus barodensis, Aleurothrixus* spp., *Amirasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii,* *Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii,* the order of *Hymenoptera* e.g. *Diprion* spp., *Hoplocampa* spp., *Lasius* spp., *Monomorium pharaonis, Vespa* spp.;

the order of *Isopoda* e.g. *Armadillidium vulgare, Oniscus asellus, Porcellio scaber;* the order of *Isoptera* e.g. *Reticulitermes* spp., *Odontotermes* spp.;

the order of *Lepidoptera* e.g. *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

the order of *Orthoptera* e.g. *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;* the order of *Siphonaptera* e.g. *Ceratophyllus* spp., *Xenopsylla cheopis;* the order of *Symphyla* e.g. *Scutigerella immaculata;* the order of *Thysanoptera* e.g. *Baliothrips biformis, Enneothrips flavens, Frankliniella* spp., *Heliothrips* spp., *Herci-*

*nothrips femoralis, Kakothrips* spp., *Rhipiphorothrips cruentatus, Scirtothrips* spp., *Taeniothrips cardamoni, Thrips* spp.;

the order of *Thysanura* e.g. *Lepisma saccharina.*

The plant parasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus* semipenetrans, *Xiphinema* spp.

The compounds of structure (I) of the invention are characterised particularly by pronounced action against aphids (e.g. *Aphis gossypii* and *Myzus persicae*) and against white fly (*Bemisia tabaci*)

The compounds of the invention can optionally also be used in certain concentrations or application amounts as herbicides, safeners, growth regulators, or as agents for improving plant properties or as microbiocides, for example as fungicides, antimycotics, bactericides, viricides (including agents against viroids) or as agents against MLO (Mycoplasma-like organism) and RLO (Rickettsia-like organism). They may also be optionally used as intermediates or precursors for the synthesis of further active compounds.

According to the invention all plants and plant parts can be treated. Plants are hereby understood to mean all plants and plant populations such as desirable and undesirable wild plants or cultigens (including naturally occurring cultigens). Cultigens can be plants that can be obtained by conventional breeding and optimisation methods or by biotechnology or genetic engineering methods or combinations of these methods, including transgenic plants and including plant varieties that are protectable or not protectable by plant varieties protection rights. Plant parts are understood to be all aboveground and subsurface parts and organs of the plants such as scion, leaf, blossom and root, including, for example, leaves, needles, stalks, stems, blossoms, fruiting bodies, fruits and seed as well as roots, bulbs, rhizomes. Harvest crops as well as vegetative and generative reproduction material, for example cuttings, bulbs, rhizomes, shoots and seed also belong to plant parts.

The treatment according to the invention of plants and plant parts with the active compound can be carried out directly or by action on their environment, habitat or storage facility by means of the normal treatment methods, for example, by immersion, spraying, evaporation, fogging, scattering, painting, injecting, and with reproductive material, in particular with seed, also by single or multiple jacketing.

The active materials of the plants can be converted into the normal formulations such as solutions, emulsions, spray powders, water- and oil-based suspensions, powders, dusting agents, pastes, soluble powders, soluble granulates, spreading granulates, suspension-emulsion concentrates, active compound impregnated natural materials, active compound impregnated synthetic materials, fertilisers and microencapsulation in polymeric materials.

These formulations can be prepared by known methods, for example by mixing the active compound with diluents, that is liquid solvents and/or solid carriers, optionally with the use of surfactants, that is emulsifiers and/or dispersants and/or foaming agents. The preparation of the formulations is carried out in suitable equipment or also before or during use.

Materials that can be used as auxiliaries are those suitable to impart special properties on the material itself and/or preparations derived from it (e.g. spray liquids, seed dressings) such as certain technical properties and/or special biological properties. Suitable auxiliaries are: diluents, solvents and carriers.

Suitable diluents are, for example, water, polar and non-polar organic liquids, for example from the class of aromatic and non-aromatic hydrocarbons (such as paraffins, alkylbenzenes, alkylnaphthalenes, chlorobenzenes), alcohols and polyols (that can be optionally substituted, etherified and/or esterified), ketones (such as acetone, cyclohexanone), esters (also fats and oils) and (poly)ethers, simple and substituted amines, amides, lactams (such as N-alkylpyrrolidones) and lactones, sulphones and sulphoxides (such as dimethyl sulphoxide).

Where water is used as diluent organic solvents, for example, can also be used as auxiliary solvents. Such suitable liquid solvents are essentially: aromatics such as xylene or toluene, or alkylnaphthalenes, chlorinated aromatics and chlorinated aliphatic hydrocarbons such as chlorobenzenes, chloroethylenes, methylene chloride, aliphatic hydrocarbons such as cyclohexane or paraffins, for example natural oil fractions, mineral and vegetable oils, alcohols such as butanol or glycol as well as their ethers and esters, ketones such as acetone, methylethylketone, methylisobutylketone or cyclohexanone, highly polar solvents such as dimethyl sulphoxide, as well as water.

Suitable as solid carriers are:

for example, ammonium salts and natural mineral powders such a kaolin, clays, talc, chalk, quartz attapulgite, montmorillonite or diatomaceous earth, and synthetic mineral powders such as highly dispersed silica, aluminium oxide and silicates, suitable as solid carriers for granulates are: for example crushed and fractionated natural minerals such as calcite, marble, pumice, sepiolite, dolomite as well as synthetic granulates of inorganic and organic flours as well as granulates from organic materials such as paper, sawdust, coconut shells, maize ears and tobacco stalks; suitable as emulsifiers and/or foaming agents are; for example non-ionogenic and anionic emulsifiers such as polyoxyethylene fatty acid esters, polyoxyethylene fatty alcohol ethers, for example alkylarylpoly-glycol ethers, alkyl sulphonates, alkyl sulphates, aryl sulphonates and protein hydrolysates; suitable as dispersant are non-ionic and/or ionic materials, for example from the class of alcohol-POE and/or POP ethers, acid and/or POP or POE esters, alkyl-aryl and/or POP or POE ethers, fat and/or POP or POE adducts, POE- and/or POP-polyol derivates, POE- and/or POP-sorbitan or sugar adducts, alkyl or aryl sulphates, sulphonates and phosphates or the respective PO ether adducts. In addition suitable oligo- or polymers, for example starting from vinylic monomers, of acrylic acid, from EO and/or PO alone or in combination with, for example (poly)alcohols or (poly)amines. In addition lignin and its sulphonic acid derivatives, simple and modified celluloses, aromatic and/or aliphatic sulphonic acids as well as their adducts with formaldehyde can be used.

Deposit builders such as carboxymethylcellulose, natural and synthetic powdery, granular or latex-like polymers can be used in the formulations, such as gum arabic, polyvinyl alcohol, polyvinyl acetate as well as natural phospholipids such as cephalins and lecithins and synthetic phospho-lipids.

Colouring agents such as inorganic pigments, for example iron oxide, titanium oxide, ferrocyan-blue and organic colouring agents, such as alizarin, azo and metallophthalocyanin dyes and trace nutrients such as iron, manganese, boron, copper, cobalt, molybdenum and zinc salts can be used.

Further additives can be aromatic principles, mineral or vegetable, optionally modified oils, waxes and nutrients (also trace nutrients) such as iron, manganese, boron, copper, cobalt, molybdenum and zinc salts.

Also included can be stabilisers such as cold stabilisers, preservatives, anti-oxidants, light-protectants or other agents that improve chemical and/or physical stability.

The formulations generally contain between 0.01 and 98 wt. % active compound, preferably between 0.5 and 90%.

The active compound of the invention can be present in its normal commercial formulations or in application forms prepared from these formulations in admixture with other active compounds such as insecticides, attractants, sterilisers, bactericides, acaricides, nematicides, fungicides, growth regulators, herbicides, safeners, fertilisers or semiochemicals.

Particularly favourable mixing partners are, for example, the following:

Fungicides:

Nucleic Acid Synthesis Inhibitors benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid Inhibitors of Mitosis and Cell Division benomyl, carbendazim, diethofencarb, fuberidazole, pencycuron, thiabendazole, thiophanate-methyl, zoxamid Inhibitor of Respiratory Complex I diflumetorim Inhibitors of Respiratory Complex II boscalid, carboxin, fenfuram, flutolanil, furametpyr, mepronil, oxycarboxin, penthiopyrad, thifluzamide Inhibitors of Respiratory Complex III azoxystrobin, cyazofamide, dimoxystrobin, enestrobin, famoxadone, fenamidone, fluoxastrobin, kresoximmethyl, metominostrobin, orysastrobin, pyraclostrobin, picoxystrobin Decouplers dinocap, fluazinam Inhibitors of ATP Production fentin acetate, fentin chloride, fentin hydroxide, silthiofam Inhibitors of Amino Acid and Protein Biosynthesis andoprim, blasticidin-S, cyprodinil, kasugamycin, kasugamycin hydrochloride hydrate, mepanipyrim, pyrimethanil Inhibitors of Signal Transduction fenpiclonil, fludioxonil, quinoxyfen Inhibitors of Fat and Membrane Synthesis chlozolinate, iprodione, procymidone, vinclozolin ampropylfos, potassium ampropylfos, edifenphos, iprobenfos (IBP), isoprothiolane, pyrazophos tolclofos-methyl, biphenyl iodocarb, propamocarb, propamocarb hydrochloride Inhibitors of Ergosterol Biosynthesis fenhexamide, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidol, nuarimol, pyrifenox, triforin, pefurazoate, prochloraz, triflumizole, viniconazole, aldimorph, dodemorph, dodemorph acetate, fenpropimorph, tridemorph, fenpropidin, spiroxamine, naftifin, pyributicarb, terbinafin Inhibitors of Cell Wall Synthesis benthiavalicarb, bialaphos, dimethomorph, flumorph, iprovalicarb, polyoxins, polyoxorim, validamycin A Inhibitors of Melanin Biosynthesis capropamide, diclocymet, fenoxanil, phtalide, pyroquilon, tricyclazole Resistance Induction acibenzolar-5-methyl, probenazole, tiadinil Multisite captafol, captan, chlorothalonil, copper salts: copper hydroxide, copper naphthenate, copper oxychloride, copper sulphate, copper oxide, oxine-copper and Bordeaux mixture, dichlofluanid, dithianon, dodin, dodin freie base, ferbam, fluorofolpet, guazatin, guazatin acetate, iminoctadin, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Unknown Mechanism amibromdol, benthiazole, bethoxazin, capsimycin, carvone, quinoline methionate, chloropicrin, cufraneb, cyflufenamide, cymoxanil, dazomet, debacarb, diclomezine, dichlorophen, dicloran, difenzoquat, difenzoquat methyl sulphate, diphenylamine, ethaboxam, ferimzone, flumetover, flusulfamide, fluopicolide, fluoroimide, hexachlorobenzene, 8-hydroxyquinoline sulphate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosin-sodium, proquinazid, pyrroInitrin, quintozen, tecloftalam, tecnazen, triazoxido, trichlamide, zarilamide and 2,3,5, 6-tetrachloro-4-(methylsulphonyl)pyridine, N-(4-chloro-2-nitrophenyl)-N-ethyl-4-methylbenzene sulphonamide, 2-amino-4-methyl-N-phenyl-5-thiazole carboxamide, 2-chloro-N-(2,3-dihydro-1,1,3-trimethyl-1H-inden-4-yl)-3-pyridine carboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)-phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridine dicarbonitrile, methyl 2-[[[cyclopropyl[(4-methoxyphenyl) imino]methyl]thio]methyl]-.alpha.-(methoxymethylen)-benzacetate, 4-chloro-alpha-propinyloxy-N-[2-[3-methoxy-4-(2-propinyloxy) phenyl]ethyl]-benzacetamide, (2S)-N-[2-[4-[3-(4-chlorophenyl)-2-propinyl]oxy]-3-methoxyphenyl-ethyl]-3-methyl-2-[(methylsulphonyl)amino]-butanamide, 5-chloro-7-(4-methylpiperidin-1-yl)-6-(2, 4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2, 3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)

oxy]phenylethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-Methoxy-3-pyridinyl)-cyclopropane carboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chlor-2-methylphenoxy)-5-fluoropyrimidin-4-yl]oxy}phenyl)-2-(methoxyimino)-N-methylacetamide Bactericides:

bronopol, dichlorophen, nitrapyrin, nickel dimethyldithiocarbamate, kasugamycin, octhilinon, furan carboxylic acid, oxytetracyclin, probenazol, streptomycin, tecloftalam, copper sulphate and other copper preparations.

Insecticides/Acaricides/Nematicides:

Acetylcholinesterase (AChE) Inhibitors carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, fonmetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate organophosphates, for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlonmephos, chlorpyrifos (-methyl/-ethyl), coumaphos, cyanofenphos, cyanophos, chlorfenvinphos, demeton-S-methyl, demeton-S-methylsulphone, dialifos, di-azinone, dichlofenthione, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fos-thiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidone, phosphocarb, Phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers pyrethroids, for example acrinathrin, allethrin (d-cis-trans, d-trans), beta-cyfluthrin, bifenthrin, bioallethrin, bioallethrin-5-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin, ZXI 8901, pyrethrins (pyrethrum)

DDT oxadiazines, for example indoxacarb

Acetylcholine Receptor Agonists/Antagonists chloronicotinyls, for example acetamiprid, clothianidin, dinotefuran, imidacloprid, nitenpyram, nithiazine, thiacloprid, thiamethoxam nicotine, bensultap, cartap Acetylcholine Receptor Modulators Spinosynes, for example spinosad GABA-Controlled Chloride Channel Antagonists Organochlorines, for example camphechlor, chlordane, endosulfan, gamma-HCH, HCH, heptachlor, lindane, methoxychlor Fiproles, for example acetoprole, ethiprole, fipronil, pyrafluprole, pyriprole, vaniliprole Chloride Channel Activators Mectins, for example avermectin, emamectin, emamectin benzoate, ivermectin, milbemycin Juvenile Hormone Mimetics, for example diofenolan, epofenonane, fenoxycarb, hydroprene, kinoprene, methoprene, pyriproxifen, triprene Ecdysone Agonists/Disruptors diacylhydrazines, for example chromafenozide, halofenozide, methoxyfenozide, tebufenozide Inhibitors of Chitin Biosynthesis Benzoylureas, for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron buprofezin cyromazine Inhibitors of Oxidative Phosphorylation, ATP Disruptors diafenthiuron organotin compounds, for example azocyclotin, cyhexatin, fenbutatin-oxide Decouplers of Oxidative Phoshorylation by Interruption of H-Proton Gradients pyrroles, for example chlorfenapyr dinitrophenols, for example binapacryl, dinobuton, dinocap, DNOC Site I Electron Transport Inhibitors METIs, for example fenazaquin, fenpyroximate, pyrimidifen, pyridaben, tebufenpyrad, tolfenpyrad hydramethylnon dicofol Site II Electron Transport Inhibitors rotenones Site III Electron Transport Inhibitors acequinocyl, fluacrypyrim Microbial Disruptors of Insect Intestinal Membrane
*Bacillus thuringiensis* strains
Inhibitors of Fat Synthesis
tetronic acids,
for example spirodiclofen, spiromesifen tetramic acids, for example spirotetramat (CAS-Reg.-No.: 203313-25-1) and 3-(2,5-dimethylphenyl)-8-methoxy-2-oxo-1-aza-spiro[4.5]dec-3-en-4-yl ethyl carbonate (alias: carbonic acid, 3-(2,5-dimethylphenyl)-8-methoxy-2-oxo-1-aza-spiro[4.5]dec-3-en-4-yl ethyl ester, CAS-Reg.-No.: 382608-10-8)

carboxamides, for example flonicamid octopaminergic agonists, for example amitraz Inhibitors of Magnesium-Stimulated ATPase, propargite benzoic acid dicarboxamides, for example flubendiamide nereistoxin analogous, for example thiocyclam hydrogen oxalate, thiosultap-sodium Biologicals, Hormones or Pheromones azadirachtin, *Bacillus* spec., *Beauveria* spec., codlemone, *Metarrhizium* spec., *Paecilomyces* spec., Thuringiensin, *Verticillium* spec.

Active Compounds with Unknown or Non-Specific Mode of Action fumigants, for example aluminium phosphide, methyl bromide, sulphuryl fluoride feeding inhibitors, for example cryolite, flonicamid, pymetrozine mite growth inhibitors, for example clofentezine, etoxazole, hexythiazox amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds such as herbicides, fertilisers, growth regulators, safeners, semiochemicals or also with agents for improving plant properties is also possible.

The active compounds of the invention can also be present in their normal commercial formulations when used as insecticides as well as in the application forms prepared from these formulations in admixture with synergists. Synergists are compounds through which the activity of the active compound can be increased without that the added synergist itself having to be active.

The active compounds of the invention can also be present in their normal commercial formulations when used as insecticides as well as in the application forms prepared from these formulations in admixture with inhibitors that reduce degradation of the active compound after use in the environment of the plants, on the surface of the plant parts or in plant tissues.

The active compound content of application forms prepared from the normal commercial formulations can vary over a wide range. The active compound content of the application form can lie within 0.00000001 to 95 wt. %, preferably between 0.00001 and 1 wt. %.

The application is carried out in a manner adapted to the application forms.

As previously described, according to the invention all plants and their parts can be treated. In a preferred embodiment wild plant species and plant varieties or plant species and plant varieties obtained by conventional biological breeding methods such as crossing or protoplast fusion and their parts are treated. In a further preferred embodiment transgenic plants and plant varieties that were produced by genetic engineering methods optionally in combination with conventional methods (genetic modified organisms) and their parts are treated. The terms “parts” and “parts of plants” or “plant parts” were explained above.

Especially preferred according to the invention plants of the respective commercially available or generally used plant varieties are treated. Plant varieties are understood to mean plants with new properties (“traits”) that have been bred by conventional breeding, by mutagenesis or by recombinant DNA techniques. These can be varieties, bio- and genotypes.

Depending upon the plant species or plant varieties, their position and growth conditions (soil, climate, vegetation period, nutrition) superadditive (“synergistic”) effects can occur by the treatment of the invention. Thus, for example, lower amounts of application and/or broadening of the activity spectrum and/or increase in the action of the substances and agents that may be used according to the invention, improved plant growth, increased tolerance toward high or low temperatures, increased tolerance toward drought or towards water or soil salt content, increased blossoming performance, simplified harvesting, acceleration in ripening, increased harvest yields, higher quality and/or nutritional value of the harvested product, better storage life and/or processing of the harvested product are possible that extend beyond actually the expected effects.

All plants that have received by genetic engineering modification genetic material which imparts particularly advantageous valuable properties (“traits”) to these plants belong to the transgenic (obtained by genetic engineering) plants or plant varieties to be preferably treated in accordance with the invention. Examples of such properties are improved plant growth, increased tolerance toward high or low temperatures, increased tolerance toward drought or toward water or soil salt content, improved blossoming performance, simplified harvesting, accelerated ripening, increased harvest yields, improved quality and/or nutritional value of the crop, better storage life and/or processing of the crop. Further and particularly highlighted examples of such properties are increased resistance of the plants toward animal pests and microbial pests, such as toward insects, mites, pathogenic plant fungi, bacteria and/or viruses as well as an increased tolerance of the plants toward certain herbicides. Examples of such transgenic plants are the important cultigens such as cereals (wheat, rice), maize, soy, potato, sugar beet, tomato, peas, and other vegetable varieties, cotton, tobacco, rape as well as fruit plants (with the fruits apple, pear, citrus fruits and grapes), whereby maize, soy, potato, cotton, tobacco and rape are especially highlighted. Properties (“traits”) especially highlighted are the increased tolerance of the plants toward insects, arachnids, nematodes and gastropods through the toxins formed in the plants, especially those that are produced in the plants (hereinafter known as “Bt plants”) by the genetic material from *Bacillus thuringiensis* (e.g. from the genes CryIA(a), CryIA(b), CryIA(c), CryIIA, CryIIIA, CryIIIB2, Cry9c Cry2Ab, Cry3Bb and CryIF as well as their combinations). Also particularly highlighted as properties ("traits") is the increased resistance of plants toward fungi, bacteria and viruses through systemically acquired resistance (SAR), systemin, phytoalexine, elicitors and resistance genes and correspondingly expressed proteins and toxins. Further particularly highlighted properties ("traits") are the increased tolerance of the plants toward certain active herbicidal compounds, for example imidazolinones, sulphonylureas, glyphosate or phosphinotricin (e.g. "PAT" gene). The respective genes imparting the desired properties ("traits") can also occur in the transgenic plants in combination with each other. Examples of such "Bt plants" are maize varieties, cotton varieties, soy varieties and potato varieties that are marketed under the trade marks YIELD GARD® (e.g. maize, cotton, soy), KnockOut® (e.g. maize), StarLink® (e.g. maize), Bollgard® (cotton), Nucotn®& (cotton) and NewLeaf® (potato). Examples of herbicide tolerant plants are maize varieties, cotton varieties and soy varieties that are marketed under the trade marks Roundup Ready® (tolerance toward glyphosate, e.g. maize, cotton, soy), Liberty Link® (tolerance toward phosphinotricin, e.g. rape), IMI® (tolerance toward imidazolinones) and STS® (tolerance toward sulphonyl ureas, e.g. maize). Also mentioned as herbicide resistant (conventionally bred for herbicide tolerance) plants are those varieties marketed under the name Clearfield® (e.g. maize). Naturally these statements also apply to plant varieties developed or marketed in the future with these genetic properties ("traits") or those developed in the future.

According to the invention the plants described can be particularly advantageously treated with the compounds of general structure I or active compound mixtures of the invention. The preferred ranges described above for the active compounds or mixtures hold also for the treatment of these plants. Particularly mentioned is plant treatment with the compounds or mixtures specially described in the present text.

The compounds of the invention are not only active against plant, hygiene and storage pests but also against animal pests in the veterinary sector (ectoparasites and endoparasites) such as hard ticks, soft ticks, mange ticks, harvest mites, flies (stinging and licking), parasitic fly larvae, lice, biting mites, chewing mites and fleas. These parasites include:

the order of *Anoplurida* e.g. *Haematopinus* spp., *Linognathus* spp., *Pediculus* spp., *Phtirus* spp., *Solenopotes* spp.;

the order of *Mallophagida* and the suborders *Amblycerina* as well as *Ischnocerina* e.g. *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.;

the order of Diptera and suborders Nematocerina as well as Brachycerina e.g. *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.; the order of *Siphonapterida* e.g. *Pulex* spp., *Ctenocephalides* spp., *Xenopsylla* spp., *Ceratophyllus* spp.;

the order of *Heteropterida* e.g. *Cimex* spp., *Triatoma* spp., *Rhodnius* spp., *Panstrongylus* spp.;

the order of *Blattarida* e.g. *Blatta orientalis*, *Periplaneta americana*, *Blattela germanica*, *Supella* spp.;

The subclass of *Acari* (*Acarina*) and the orders Meta- and Mesostigmata e.g. *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.;

the order of *Actinedida* (Prostigmata) and *Acaridida* (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The compounds of the invention of structure (I) are also suitable for the control of arthropods that affect agricultural animals such as cattle, sheep, goats, horses, pigs, donkeys, camels, buffalo, rabbits, chickens, turkeys, ducks, geese, bees, miscellaneous domestic animals such as dogs, cats, cage birds, aquarium fish as well as so-called experimental animals such as hamsters, guinea pigs, rats and mice. By control of these arthropods death rates and performance loss (in meat, milk, wool, hides, eggs, honey, etc.) will be reduced so that a more economic and simpler animal husbandry is possible by the use of the compounds of the invention.

The use of the active compounds in veterinary sector and animal husbandry is carried out by known means by enteric administration in the form of, for example, tablets, capsules, drinks, drenches, granulates, pastes, boluses, the feed-through process, suppositories, by parenteral administration by, for example, injection (intramuscular, subcutaneous, intravenous, intraperitoneal, amongst others), implants, by nasal application, by dermal administration in the form of, for example, dipping, spraying, pour-on and spot-on, washing, powdering and with the help of appliances containing the active compound such as collars, ear markers, tail markers, limb bands, halters, marking devices, etc.

During use in cattle, poultry, domestic animals, etc., the active compounds of structure (1) can be used as formulations (for example, powders, emulsions, flowable agents) that contain the active compounds in an amount of 1 to 80 wt. %, directly or after 100 to 10,000 times dilution or as a chemical bath.

Moreover it has been found that the compounds of the invention exhibit high insecticidal action against insects that destroy technical materials.

As examples and preferably—but not limiting—the following insects are named:

beetles such as *Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus*, *Sinoxylon* spec. *Dinoderus minutus*; hymenoptera such as *Sirex juvencus*, *Urocerus gigas*, *Urocerus gigas taignus*, *Urocerus augur*; termites such as *Kalotermes flavicollis*, *Cryptotermes brevis*, *Heterotermes indicola*, *Reticulitermes* flavipes, Reticulitermes santonensis, Reticulitermes lucifugus, Mastotermes darwiniensis, Zootermopsis nevadensis, Coptotermes formosanus;

silverfish such as Lepisma saccharina.

Within the present context technical materials are understood to mean non-living materials such as preferably plastics, adhesives, glues, paper and cardboard, leather, wood, wood fabrication products and paints.

The ready-to-use agents can optionally include further insecticides and optionally one or more fungicides.

In respect of possible admixture partners reference is made to the above-named insecticides and fungicides.

At the same time the compounds of the invention can be used for protection against fouling of objects, especially ships' hulls, screens, nets, buildings, wharfs and signal installations that come into contact with sea or brackish water.

Moreover, the compounds of the invention can be used in combination with other active compounds as antifouling agents.

The active compounds are suitable for the control of animal pests in household, hygiene and storage protection, especially insects, arachnids and mites that appear in enclosed spaces such as apartments, factory halls, offices, vehicle cabins, etc. They can be used alone or in combination with other active compounds and auxiliaries in domestic insecticidal products for the control of these pests. They are active against sensitive and resistant species as well as against all development stages. These pests include:

the order of *Scorpionidea* e.g. *Buthus occitanus*;

the order of *Acarina* e.g. *Argas persicus*, *Argas reflexus*, *Bryobia* ssp., *Dermanyssus gallinae*, *Glyciphagus domesticus*, *Ornithodorus moubat*, *Rhipicephalus sanguineus*, *Trombicula alfreddugesi*, *Neutrombicula autumnalis*, *Dermatophagoides pteronissimus*, *Dermatophagoides forinae*;

the order of *Araneae* e.g. *Aviculariidae*, *Araneidae*;

the order of *Opiliones* e.g. *Pseudoscorpiones chelifer*, *Pseudoscorpiones cheiridium*, *Opiliones phalangium*;

the order of *Isopoda* e.g. *Oniscus asellus*, *Porcellio scaber*;

the order of *Diplopoda* e.g. *Blaniulus guttulatus*, *Polydesmus* spp.; the order of *Chilopoda* e.g. *Geophilus* spp.; the order of *Zygentoma* e.g. *Ctenolepisma* spp., *Lepisma saccharina*, *Lepismodes inquilinus*; the order of *Blattaria* e.g. *Blatta orientalies*, *Blattella germanica*, *Blattella asahinai*, *Leucophaea maderae*, *Panchlora* spp., *Parcoblatta* spp., *Periplaneta australasiae*, *Periplaneta americana*, *Periplaneta brunnea*, *Periplaneta fuliginosa*, *Supella longipalpa*;

the order of *Saltatoria* e.g. *Acheta domesticus*;

the order of *Dermaptera* e.g. *Forficula auricularia*;

the order of *Isoptera* e.g. *Kalotermes* spp., *Reticulitermes* spp.;

the order of *Psocoptera* e.g. *Lepinatus* spp., *Liposcelis* spp.;

the order of *Coleoptera* e.g. *Anthrenus* spp., *Attagenus* spp., *Dermestes* spp., *Latheticus oryzae*, *Necrobia* spp., *Ptinus* spp., *Rhizopertha dominica*, *Sitophilus granarius*, *Sitophilus oryzae*, *Sitophilus zeamais*, *Stegobium paniceum*;

the order of *Diptera* e.g. *Aedes aegypti*, *Aedes albopictus*, *Aedes taeniorhynchus*, *Anopheles* spp., *Calliphora erythrocephala*, *Chrysozona pluvialis*, *Culex quinquefasciatus*, *Culex pipiens*, *Culex tarsalis*, *Drosophila* spp., *Fannia canicularis*, *Musca domestica*, *Phlebotomus* spp., *Sarcophaga carnaria*, *Simulium* spp., *Stomoxys calcitrans*, *Tipula paludosa*;

the order of *Lepidoptera* e.g. *Achroia grisella*, *Galleria mellonella*, *Plodia interpunctella*, *Tinea cloacella*, *Tinea pellionella*, *Tineola bisselliella*;

the order of *Siphonaptera* e.g. *Ctenocephalides canis*, *Ctenocephalides felis*, *Pulex irritans*, *Tunga penetrans*, *Xenopsylla cheopis*;

the order of *Hymenoptera* e.g. *Camponotus herculeanus*, *Lasius fuliginosus*, *Lasius niger*, *Lasius umbratus*, *Monomorium pharaonis*, *Paravespula* spp., *Tetramorium caespitum*;

the order of *Anoplura* e.g. *Pediculus humanus capitis*, *Pediculus humanus corporis*, *Pemphigus* spp., *Phylloera vastatrix*, *Phthirus pubis*;

the order of *Heteroptera* e.g. *Cimex hemipterus*, *Cimex lectularius*, *Rhodinus prolixus*, *Triatoma infestans*.

The use in the domestic insecticide sector is carried out alone or in combination with other suitable active compounds such as phosphates, carbamates, pyrethroids, neonicotinoids, growth regulators or active compounds from other know classes of insecticides.

Use is carried out with aerosols, non-pressurised spray agents, e.g. pump and dusting sprays, nebulisers, misters, foamers, gels, evaporation products with evaporation platelets of cellulose or plastic, liquid evaporators, gel and membrane evaporators, propeller-driven evaporators, non-energy or passive evaporation systems, fly papers, fly traps, and fly gels, as granulates or dusts, in scatter bait or bait stations.

PREPARATION EXAMPLES

Example I-1

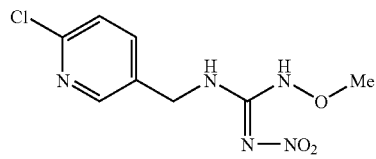

2.60 g (10.0 mMol) N-nitro-N'-(2-chloropyrid-5-ylmethyl)-S-methylisothiourea and 0.84 g (10.0 mMol) O-methylhydroxylamine hydrochloride are stirred with 1.10 g (11 mMol) triethylamine in a mixture of 60 ml ethanol/water (1:1) for ca. 18 hours at 50° C. to 55° C. The reaction mixture is then evaporated under reduced pressure and separated by column chromatography.

1.4 g (54% of theory) N-methoxy-N'-(2-chloropyrid-5-ylmethyl)nitroguanidine are obtained.

$C_8H_{10}ClN_5O_3$ (359.6)

LC-MS m/z (%)=260 (MH$^+$, 100).

$^1$H NMR (600 MHz, DMSO-d$_6$, δ)=3.72 (3H, —O—CH$_3$); 4.39 (2H, —CH$_2$—Cl—Py); 7.51; 7.78; 8.35 (3×1H, Cl—Py—CH—); 8.49; 11.82 (2×1H, —NH) ppm.

$^{13}$C with $^1$H decoupling (CPD) and $^1$H with $^{13}$C correlation (HMQC, HMBC; 600 MHz, DMSO-d$_6$, δ)=41.1 (—NH—CH$_2$—Cl—Py); 64.1 (—O—CH$_3$); 124.2 (Cl—Py-CH—); 134.1 (Cl—Py-C—); 139.1 (Cl—Py-CH—); 149.2 (Cl—Py-CH—); 149.1 (Cl—Py-C—Cl); 156.6 (—C=N—NO$_2$) ppm.

$^1$H/$^{15}$N correlation (HMBC, 600 MHz, DMSO-d$_6$, δ)=–209.9 (—NH—O—); -295.2 (—NH—CH$_2$—); -74.1 (Cl—Py—N—) ppm.

Analogous to preparation example 1 and in accordance with the general description of the preparation methods of the invention the compounds of structure (I) listed in Table 1 can, for example, also be prepared.

TABLE 1

(I)

$$\underset{R^1}{\overset{R^4}{\underset{|}{A}}}\overset{R^3}{\underset{N-Z}{N}}O^{R^2}$$

| Ex.-no. | A | $R^1$ | $R^2$ | $R^3$ | $R^4$ | Z | Physical data |
|---|---|---|---|---|---|---|---|
| I-2 | 2-Cl-5-pyridyl | H | $CH_2CH_3$ | H | H | $NO_2$ | $^{13}$C NMR (CDCl$_3$, 400 MHz); 13.3 (CH$_3$); 41.7 (HN—CH$_2$); 72.8 (O—CH$_2$); 124.3, 138.8; 149.1 (=CH—, hetaryl); 150.7 (Cl—C=, hetaryl); 132.1 (—C=, hetaryl); 157.5 (C=N—NO$_2$) ppm |
| I-3 | 2-Cl-5-pyridyl | H | $CH_2CH_2CH_2CH_3$ | H | H | $NO_2$ | logP = 2.06 (pH = 2) |
| I-4 | 2-Cl-5-pyridyl | H | H | H | H | $NO_2$ | $^{13}$C NMR (DMF-d$_7$, 400 MHz); 41.6 (HN—CH$_2$); 124.6, 139.6; 149.9 (=CH—; hetaryl); 149.9 (Cl—C=, hetaryl); 135.1 (—C=, hetaryl); 158.9 (C=N—NO$_2$) ppm |
| I-5 | 2-Cl-thiazol-5-yl | H | $CH_3$ | H | H | $NO_2$ | logP = 1.13 (pH = 2) |
| I-6 | 2-Cl-thiazol-5-yl | H | $CH_2CH_3$ | H | H | $NO_2$ | logP = 1.42 (pH = 2) |
| I-7 | 2-Cl-5-pyridyl | H | $CH_3$ | $CH_3$ | H | $NO_2$ | logP = 0.67 (pH = 2) |
| I-8 | 2-Cl-thiazol-5-yl | H | $CH_3$ | H | $CH_3$ | $NO_2$ | logP = 0.75 (pH = 2) |
| I-9 | 2-Cl-5-pyridyl | H | $CH_3$ | H | $CH_3$ | $NO_2$ | logP = 0.96 (pH = 2) |

Example (I-10)

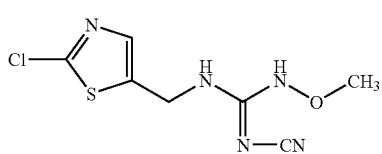

N-Methoxyamino-N'-(2-chloro-1,3-thiazol-5-yl)cyanoguanidine 169.2 mg (2.0 mMol) O-methylhydroxylamine hydrochloride and 500 mg (2.0 mMol) S-Methyl-N-cyano-N'-(2-chloro-1,3-thiazol-5-yl)isothiourea are added to 10 ml ethanol and treated with 0.31 ml (2.2 mMol) triethylamine and 10.0 ml water. The reaction mixture is then stirred for three days at 40° C., two further days at 60° C. and one day at 80° C. At the end of the reaction the ethanol is distilled off under reduced pressure and the residue is extracted three times with ethyl acetate. After drying the organic phase is evaporated to dryness under reduced pressure and the residue is purified by preparative HPLC. 16.6 mg (3.1%) N-methoxyamino-N'-(2-chloro-1,3-thioazol-5-yl)cyanoguanidine are obtained.

$C_7H_8ClN_5OS$ (245.7)

LC-MS m/z (%)=247 (MH$^+$)

Example (I-11)

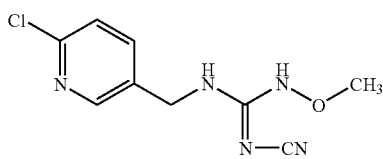

N-Methoxyamino-N'-(6-chloropyrid-3-yl)cyanoguanidine 169.2 mg (20 mMol) O-methylhydroxylamine hydrochloride and 2.0 g (8.3 mMol) S-methyl-N-cyano-N'-(6-chloropyrid-3-yl)isothiourea are added to 50 ml ethanol and treated with 1.27 ml (9.1 mMol) triethylamine and 50.0 ml water. The reaction mixture is then stirred for ca. 18 hours at 60° C. under a protective gas (argon). At the end of the reaction the ethanol is distilled off under reduced pressure and the aqueous residue is extracted three times with chloroform. After drying the organic phase is evaporated to dryness under reduced pressure and the residue is purified by preparative HPLC. 13.5 mg (0.7%) N-methoxyamino-N'-(6-chloropyrid-3-yl)cyanoguanidine are obtained.

$C_9H_{10}ClN_5OS$ (239.7)

LC-MS m/z (%)=239 (M$^+$)

Starting Materials of Structure (II):

Example (II-1)

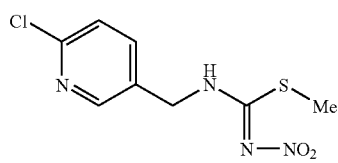

Stage 1

S-Methyl-N-nitro-N'-phthaloylisothiourea 24.7 g (0.18 mol) S-methyl-N-nitroisothiourea (cf. L. Fishbein, J. A. Gallaghan, J. Am. Chem. Soc. 76, 1877, 1954) are stirred in 345 ml pyridine and treated dropwise at 0° C. to 5° C. with 71.6 g (0.35 mol) phthaloyl chloride. After stirring for 30 minutes the whole reaction mixture is added to an ice water/hydrochloric acid mixture and stirred well. The precipitated solid is separated and stirred in hot ethanol.

After separation of the solid 36.7 g (39% of theory) S-methyl-N-nitro-N'-phthaloyl-isothiourea are obtained that can be used for further conversion without further purification.

Stage 2

23.3 g (0.088 mol) S-methyl-N-nitro-N'-phthaloylisothiourea are added to 250 ml acetonitrile and treated with a solution of 12.5 g (0.088 mol) 3-aminomethyl-6-chloropyridine in 50 ml acetonitrile at 0° C. to 5° C. over 30 minutes. The mixture is then stirred for a further 30 minutes at 0° C. to 5° C. and ca. 18 hours at room temperature (ca. 20° C.). The precipitated solid is separated and stirred in a mixture of methanol/ethyl acetate (1:1) (undissolved residue: 3.9 g). The organic solution is extracted with ethyl acetate/5% sodium hydroxide solution to give a further 11.3 g (49% of theory) N-(6-chloro-pyrid-3-yl-methyl)-S-methyl-N'-nitroisothiourea that can be used directly for further conversion.

N-Methoxy-N'-nitroguanidine

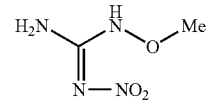

27.0 g (0.20 mol) S-methyl-N-nitroisothiourea (cf. L. Fishbein, J. A. Gallaghan J. Am. Chem. Soc. 76, 1877, 1954) and 16.7 g (0.20 mol) O-methylhydroxylamine hydrochloride are stirred in 400 ml water, treated with 22.2 g (0.22 mol) triethylamine and stirred for 16 hours at 55° C. After just 2 to 3 hours mercaptan formation subsides. The whole reaction mixture is then evaporated to dryness under reduced pressure and stirred with a mixture of 100 ml water/200 ml methylene chloride.

7.6 g (28.4% of theory) N-methoxy-N'-nitro-guanidine is obtained as a pale yellow powder.

After addition of sodium hydrogen carbonate solution and extraction with methylene chloride 3.0 g (12.5% of theory) N-methoxy-5-methyl-isothiourea can be isolated from the mother liquor as byproduct.

$C_2H_6N_4O_3$ (134.0)

LC-MS m/z (%)=135 (MH$^+$, 100)

m.p.: 138-142° C.

$^1$H NMR (600 MHz, DMF-d$_7$, δ)=3.78 (3H, OCH$_3$); 8.03 (2H, br., NH$_2$); 11.36 (1H, NH) ppm.

$^{13}$C with $^1$H decoupling (CPD, 100 MHz, DMF-d$_7$, δ)=64.5 (OCH$_3$); 161.4 (C=N) ppm.

$^1$H/$^{15}$N correlation (HMBC, 600 MHz, DMF-d$_7$, δ)=−212.9 (NH—OCH$_3$) ppm.

N-Methoxy-5-methylisothiourea $C_3H_8N_2OS$ (120.1)

LC-MS m/z (%)=121 (MH$^+$, 100)

$^1$H NMR (600 MHz, DMF-d$_7$, δ)=2.25 (3H, SCH$_3$); 3.61 (3H, OCH$_3$); 6.02 (2H, br., —NH$_2$) ppm.

$^{13}$C with $^1$H decoupling (CPD) and $^1$H with $^{13}$C correlation (HMBC, 600 MHz, DMSO-d$_6$, δ)=12.8 (SCH$_3$); 60.6 (OCH$_3$); 151.3 (C=N) ppm.

$^1$H/$^{15}$N-correlation (HMBC, 600 MHz, DMSO-d$_6$, δ)=−308.2 (NH$_2$); −86.7 (C=N) ppm.

Example (II-2)

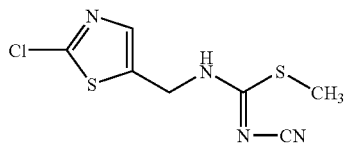

S-Methyl-N-cyano-N'-(2-chloro-1,3-thiazol-5-yl)
isothiourea 500 mg (3.36 mMol) 5-chloromethyl-2-chloro-1,3-thiazole are stirred in 80 ml ethanol and at 0° C. treated dropwise with an ethanolic solution of 738 mg (5.0 mMol) dimethyl N-cyano-dithiocarbamate. The reaction mixture is then stirred for a further 18 hours at room temperature, the whole reaction mixture is evaporated under reduced pressure and the residue dissolved in 30 ml hot ethanol and filtered. After cooling the crystals are separated and dried on a porous plate. 687.5 mg (75.4%) S-methyl-N-cyano-N'-(2-chloro-1,3-thiazol-5-yl)isothiourea are obtained.

$C_7H_7ClN_4S_2$ (246.7)

LC-MS m/z (%)=247 (M$^+$)

$^1$H NMR (400 MHz, CD$_3$CN, δ)=2.51 (3H, SCH$_3$); 4.63 (2H, NH—CH$_2$); 7.17 (2H, br., NH); 7.49 (1H, thiazol-H) ppm.

Example (II-3)

In an analogous manner S-methyl-N-cyano-N'-(6-chloro-pyrid-3-yl)isothiourea is obtained $C_9H_9ClN_4S$ (240.7)

LC-MS m/z (%)=241 (M$^+$)

Example A

*Myzus persicae* Test

| Solvent: | 7 parts by weight dimethylformamide |
|---|---|
| Emulsifier: | 1 part by weight alkylarylpolyglycol ether |

To prepare a suitable active compound preparation 1 part by weight of the active compound is mixed with the given amount of solvent and the given amount of emulsifier and the concentrate is diluted to the desired concentration with water.

Cabbage leaves (*Brassica oleracea*) that are highly infested with the green peach aphid (*Myzus persicae*) are treated by immersion in the active compound preparation at the desired concentration.

After the desired time the death rate in % is determined. Here 100% means that all aphids were killed; 0% means that no aphids were killed.

The compounds of preparation examples I-1 and I-5, for example, showed good activity in this test.

TABLE A

Plant damaging insects

*Myzus* test

| Active compounds | Active compound concentration in ppm | Death rate in % after 6$^d$ |
|---|---|---|
|  (I-1) | 1000 | 98 |
|  (I-5) | 1000 | 98 |

Example B

Myzus Test

Spray Treatment

| Solvent: | 78 parts by weight acetone |
|---|---|
| | 1.5 parts by weight dimethylformamide |
| Emulsifier: | 0.5 parts by weight alkylarylpolyglycol ether |

To prepare a suitable active compound preparation 1 part by weight of the active compound is mixed with the given amount of solvent and the given amount emulsifier and the concentrate is diluted to the desired concentration with water.

Chinese cabbage leaves (*Brassica pekinensis*) infested with all stages of the green peach aphid (*Myzus persicae*) were sprayed with an active compound preparation at the desired concentration.

After the desired time the death rate in % is determined. Here 100% means that all aphids were killed; 0% means that no aphids were killed.

The compound of preparation example 1-2, for example, showed good activity in this test.

TABLE B

Plant damaging insects

*Myzus* test (Spray treatment)

| Active compounds | Active compound concentration in ppm | Death rate in % after 4$^d$ |
|---|---|---|
| 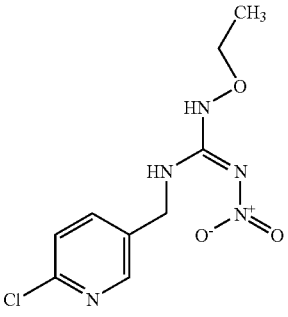 (I-2) | 500 | 100 |

Example C

*Myzus persicae* Test

Soil Application

| Solvent: | 4 parts by weight acetone |
|---|---|
| Emulsifier: | 1 part by weight alkylarylpolyglycol ether |

To prepare a suitable active compound preparation 1 part by weight of the active compound is mixed with the given amount of solvent and the given amount of emulsifier and the concentrate is diluted to the desired concentration with water.

The active compound preparation is mixed with soil. The concentration given relates to the amount of active compound per unit volume soil (mg/l=ppm). The treated soil is filled into pots and planted with one pepper plant (*Capsicum annuum*). After one week infection is carried out with the green peach aphid (*Myzus persicae*).

After the desired time the activity in % is determined. Here 100% means that all aphids were killed; 0% means that no aphids were killed.

The compounds of preparation examples I-1 and I-5, for example, showed good activity in this test.

TABLE C

Plant damaging insects

*Myzus persicae* test (soil application)

| Active compounds | Active compound concentration in ppm | Death rate in % after 7$^d$ |
|---|---|---|
| 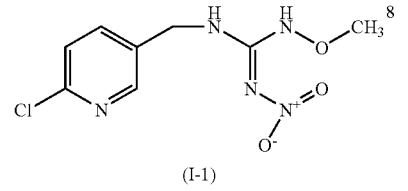 (I-1) | 8 | 100 |
| 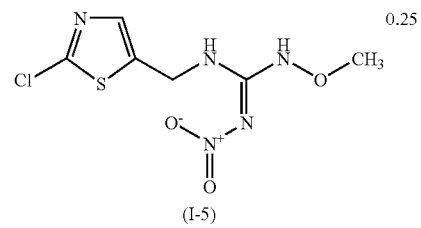 (I-5) | 0.25 | 85 |

Example D

*Aphis gossypii* Test

Soil Application

| Solvent: | 4 parts by weight acetone |
|---|---|
| Emulsifier: | 1 part by weight alkylarylpolyglycol ether |

To prepare a suitable active compound preparation 1 part by weight of the active compound is mixed with the given amount of solvent and the given amount of emulsifier and the concentrate is diluted to the desired concentration with water.

The active compound preparation is mixed with soil. The concentration given relates to the amount of active compound per unit volume soil (mg/l=ppm). The treated soil is filled into pots and planted with one cotton plant (*Gossypium hirsutum*). After a week infection is carried out with the cotton aphid (*Aphis gossypii*).

After the desired time the death rate in % is determined. Here 100% means that all aphids were killed; 0% means that no aphids were killed.

The compounds of preparation examples I-1 and I-5, for example, showed good activity in this test.

TABLE D

Plant damaging insects
*Aphis gossypii* test
(soil application)

| Active compounds | Active compound concentration in ppm | Death rate in % after 7$^d$ |
|---|---|---|
| (I-1) [6-chloropyridin-3-ylmethyl compound structure] | 8 | 100 |
| (I-5) [2-chlorothiazol-5-ylmethyl compound structure] | 0.25 | 80 |

Example E

*Bemisia tabaci* Test

Resistant Strain

| Solvent: | 10 parts by weight acetone |
|---|---|
| Emulsifier: | 0.2 parts by weight Triton X-100 |

To prepare a suitable active compound preparation 1 part by weight of the active compound is mixed with the given amount of solvent and the given amount of emulsifier and the concentrate is diluted to the desired concentration with water containing emulsifier.

Leaf sections of cotton plants (*Gossypium hirsutum*) are treated by immersion in the active compound preparation at the desired concentration and after drying of the coating are infected with adults of the white fly (*Bemisia tabaci*, resistant strain).

After the desired time the death rate in % is determined. Here 100% means that all animals were killed; 0% means that no animals were killed.

The compounds of preparation example I-5, for example, showed good activity in this test.

TABLE E

Plant damaging insects
*Bemisia tabaci* test
(resistant strain)

| Active compounds | Active compound concentration in ppm | Death rate in % after 3$^d$ |
|---|---|---|
| (I-5) [2-chlorothiazol-5-ylmethyl compound structure] | 1000 | 93 |

Example F

Myzus Test

Spray Treatment

| Solvent: | 78 parts by weight acetone |
|---|---|
| | 1.5 parts by weight dimethylformamide |
| Emulsifier: | 0.5 parts by weight alkylarylpolyglycol ether |

To prepare a suitable active compound preparation 1 part by weight of the active compound is mixed with the given amount of solvent and the given amount of emulsifier and the concentrate is diluted to the desired concentration with water containing emulsifier.

China cabbage leaf sections (*brassica pekinensis*) that are infected with all stages of the green peach aphid (*Myzus persicae*) are sprayed with an active compound preparation at the desired concentration.

After the desired time the activity in % is determined. Here 100% means that all aphids were killed; 0% means that no aphids were killed.

TABLE F

Plant damaging insects
*Myzus* test
(Spray treatment)

| Active compounds | Active compound concentration g a.i./ha | Activity in % after 5$^d$ |
|---|---|---|
| (I-11) [6-chloropyridin-3-ylmethyl cyanoimino compound structure] | 500 | 100 |

TABLE F-continued

Plant damaging insects
*Myzus* test
(Spray treatment)

| Active compounds | Active compound concentration g a.i./ha | Activity in % after 5$^d$ |
|---|---|---|
| 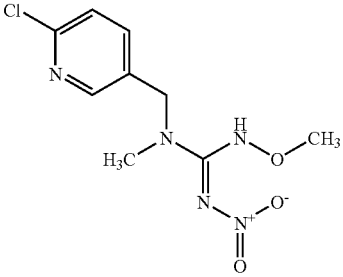<br>(I-9) | 500 | 100 |

Example G

*Spodoptera frugiperda* Test

| Solvent: | 7 parts by weight dimethylformamide |
|---|---|
| Emulsifier: | 2 parts by weight alkylarylpolyglycol ether |

To prepare a suitable active compound preparation 1 part by weight of the active compound is mixed with the given amount of solvent and the given amount of emulsifier and the concentrate is diluted to the desired concentration with water containing emulsifier.

Cabbage leaves (*Brassica oleracea*) are treated by immersion in the active compound preparation at the desired concentration and infected with caterpillars of the fall army worm (*Spodoptera frugiperda*) while the leaves are still wet.

After the desired time the death rate in % is determined. Here 100% means that all caterpillars were killed; 0% means that no caterpillars were killed.

TABLE G

Plant damaging insects
*Spodoptera frugiperda* test

| Active compounds | Active compound concentration g a.i./ha | Death rate in % after 7$^d$ |
|---|---|---|
| 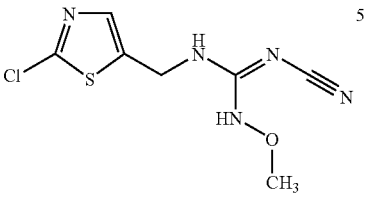<br>(I-10) | 500 | 100 |

Example H

*Frankliniella occidentalis* Test

| Solvent: | 7 parts by weight dimethylformamide |
|---|---|
| Emulsifier: | 10 parts by weight alkylarylpolyglycol ether |

To prepare a suitable active compound preparation 1 part by weight of the active compound is mixed with the given amount of solvent and the given amount of emulsifier and the concentrate is diluted to the desired concentration with water containing emulsifier.

Cotton plants (*Gossypium hirsutum*) are treated by spraying with the active compound preparation at the desired concentration and infected with a mixed thrips population (*Frankliniella occidentalis*).

After the desired time the death rate in % is determined. Here 100% means that all thrips were killed; 0% means that no thrips were killed.

TABLE H

Plant damaging insects
*Frankliniella occidentalis* test

| Active compounds | Active compound concentration in ppm | Death rate in % after 14$^d$ |
|---|---|---|
| 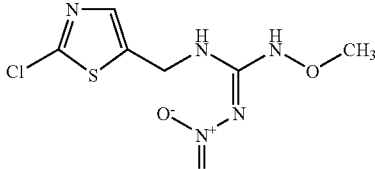<br>(I-5) | 100 | 90 |

The invention claimed is:

1. A compound of formula (I)

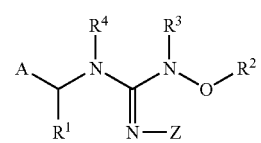

in which

A is thiazolyl or pyridyl, each of which is optionally substituted by halogen or $C_1$-$C_3$-alkyl, $R^1$ is hydrogen or methyl, $R^2$ is hydrogen or methyl, ethyl or n-propyl, $R^3$ is hydrogen or methyl, $R^4$ is hydrogen, methyl, ethyl or cyclopropyl, and Z is cyano or nitro.

2. A compound according to claim 1, wherein
A is 2-chloropyridin-5-yl or 2-chloro-1,3-thiazol-5-yl,
$R^1$ is hydrogen,
$R^2$ is methyl or ethyl,
$R^3$ is hydrogen,
$R^4$ is hydrogen, and
Z is nitro.

3. A process for the preparation of a compound according to claim 1, comprising reacting an isothiourea of formula (II) or an acid adduct of an isothiourea of formula (II)

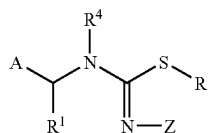
(II)

in which
A, $R^1$, $R^4$ and Z are as described in claim 1 and
R is alkyl, with an oxyamine of formula (III)

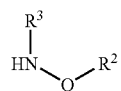
(III)

in which
$R^2$ and $R^3$ are as described in claim 1,
optionally in the presence of a basic reaction auxiliary and optionally in the presence of a diluent.

4. A composition for the control of animal pests comprising at least one compound according to claim 1, and a diluent, a surfactant, or a combination thereof.

5. A process for the preparation of a composition comprising at least one compound according to claim 1, and a diluent, a surfactant, or a combination thereof, comprising mixing said compound with a diluent, a surfactant, or a combination thereof.

* * * * *